(12) United States Patent
Zeun et al.

(10) Patent No.: US 8,349,820 B2
(45) Date of Patent: Jan. 8, 2013

(54) USE OF ESTRADIOL VALERATE OR 17β-ESTRADIOL IN COMBINATION WITH DIENOGEST FOR ORAL THERAPY TO MAINTAIN AND/OR INCREASE FEMININE LIBIDO

(75) Inventors: Susan Zeun, Berlin (DE); Holger Zimmermann, Falkensee (DE); Susanne Parke, Berlin (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 973 days.

(21) Appl. No.: 11/873,595

(22) Filed: Oct. 17, 2007

(65) Prior Publication Data

US 2008/0125401 A1 May 29, 2008

Related U.S. Application Data

(60) Provisional application No. 60/917,154, filed on May 10, 2007.

(30) Foreign Application Priority Data

Oct. 20, 2006 (EP) .................................. 06022091
May 10, 2007 (EP) .................................. 07009373

(51) Int. Cl.
*A61K 31/56* (2006.01)
(52) U.S. Cl. ........................................... 514/170
(58) Field of Classification Search .................... 514/170
See application file for complete search history.

(56) References Cited

U.S. PATENT DOCUMENTS

| | | | |
|---|---|---|---|
| 3,639,600 A | 2/1972 | Hendrix et al. |
| 3,795,734 A | 3/1974 | Rochefort |
| 3,957,982 A | 5/1976 | Lachnit-Fixson et al. |
| 4,066,757 A | 1/1978 | Pasquale et al. |
| 4,378,356 A | 3/1983 | DeJager |
| 4,390,531 A | 6/1983 | Edgren et al. |
| 4,530,839 A | 7/1985 | Pasquale et al. |
| 4,544,554 A | 10/1985 | Pasquale et al. |
| 4,616,006 A | 10/1986 | Pasquale et al. |
| 4,621,079 A | 11/1986 | Lachnit-Fixson et al. |
| 4,628,051 A | 12/1986 | Pasquale et al. |
| 4,921,843 A | 5/1990 | Pasquale |
| 5,280,023 A | 1/1994 | Ehrlich et al. |
| 5,583,129 A | 12/1996 | Spona et al. |
| 5,633,242 A | 5/1997 | Oettel et al. |
| 5,858,405 A | 1/1999 | Gast et al. |
| 6,027,749 A | 2/2000 | Schmidt-Gollwitzer et al. |
| 6,133,251 A | 10/2000 | Dittgen et al. |
| 6,312,722 B1 | 11/2001 | Schmidt-Gollwitzer et al. |
| 6,670,350 B1 | 12/2003 | Oettel et al. |
| 6,782,282 B2 | 8/2004 | Bielefeldt et al. |
| 6,884,793 B2 | 4/2005 | Dittgen et al. |
| 6,987,101 B1 | 1/2006 | Nashed |
| 2002/0107229 A1 | 8/2002 | Dittgen et al. |
| 2004/0266745 A1 | 12/2004 | Schwanitz et al. |
| 2005/0032756 A1 * | 2/2005 | Dittgen et al. ............... 514/170 |
| 2005/0282790 A1 | 12/2005 | Nashed |
| 2006/0135496 A1 | 6/2006 | DiLiberti et al. |
| 2007/0111977 A1 | 5/2007 | Zeun et al. |
| 2007/0259840 A1 | 11/2007 | Endrikat et al. |
| 2008/0125401 A1 | 5/2008 | Zeun et al. |

FOREIGN PATENT DOCUMENTS

| | | |
|---|---|---|
| BE | 823 689 | 6/1975 |
| CA | 1 090 256 | 11/1980 |
| CA | 2140011 A1 | 1/1994 |
| DE | 2 431 704 | 1/1976 |
| DE | 2 645 307 | 4/1978 |
| DE | 3 341 638 | 5/1984 |
| DE | 3 347 125 | 7/1985 |
| DE | 41 04 385 C1 | 8/1992 |
| DE | 42 24 534 A1 | 1/1994 |
| DE | 43 08 406 C1 | 6/1994 |
| DE | 4 339 934 | 11/1994 |
| DE | 43 13 926 A1 | 11/1994 |
| DE | 44 29 374 C1 | 2/1996 |
| EP | 0 036 229 | 9/1981 |
| EP | 0 226 679 | 7/1987 |
| EP | 0 253 607 | 1/1988 |
| EP | 0 378 373 A2 | 7/1990 |
| EP | 0 491 415 B1 | 6/1992 |
| EP | 0 696 454 A2 | 2/1996 |
| EP | 0 770 388 A1 | 5/1997 |
| EP | 0 911 029 B1 | 4/2002 |
| EP | 0 835 114 B1 | 5/2003 |
| EP | 1 462 106 | 9/2004 |
| EP | 1 787 649 | 5/2007 |
| GB | 1 578 240 | 11/1980 |
| NL | 6 911 920 | 2/1970 |
| WO | WO-1992 013539 | 8/1992 |
| WO | WO 95/07081 A1 | 3/1995 |
| WO | WO-98 04246 | 2/1998 |
| WO | WO-98 04265 | 2/1998 |
| WO | WO 98/04268 | 2/1998 |
| WO | WO-98 04269 | 2/1998 |
| WO | WO 98/27929 A2 | 7/1998 |
| WO | WO-02 22110 | 3/2002 |

(Continued)

OTHER PUBLICATIONS

Davis et al., Annual Review of Sex Research, 2004;15:297-320.*

(Continued)

*Primary Examiner* — San-Ming Hui
(74) *Attorney, Agent, or Firm* — Millen, White, Zelano & Branigan, PC

(57) ABSTRACT

The invention relates to the use, optionally together with oral contraception, of estradiol valerate or 17β-estradiol in combination with 17α-cyanomethyl-17-β-hydroxyestra-4,9-dien-3-one (dienogest) in a multistage or single-stage combination preparation for oral therapy to maintain and/or increase feminine libido.

The total number of daily dose units of the multistage combination and of a pharmaceutically harmless placebo or a single-stage combination and optionally the pharmaceutically harmless placebo-containing or placebo- and hormone-free daily dose units amounts to 28 daily dose units.

6 Claims, No Drawings

FOREIGN PATENT DOCUMENTS

| WO | WO 2004/112797 A1 | 12/2004 |
|---|---|---|
| WO | 2005/102247 | 11/2005 |
| WO | WO 2005/102247 A2 | 11/2005 |
| WO | 2007/002862 | 1/2007 |
| WO | WO 2007/002862 A2 | 1/2007 |
| ZA | 8509 892 A | 7/1986 |

OTHER PUBLICATIONS

Blitzer: Kontrazeption und Sexualitaet [Contraception and Sexuality], Therapeutische Umschau, vol. 51, 1994, Issue 2, pp. 110-114.
M Dei, et al . "Sex Steroids and Libido" The European Journal of Contraception and Reproductive Health Care, 1997, pp. 253-258.
Duran M. et al., "Effectiveness of Estradiol Valerato/Dienogest in the Tratment of Sexual Function During Menopause (Venus Study)", Acta Ginecologica 2006 (Spain), vol. 63, Nr. 1, Seiten 1-8, Abstract.
Osmanagaoglu M.A. et., "Effect of Different Preparations of Hormone Therapy on Sexual Dysfunction in Naturally Postmenopausal Women", Climacteric: Ther Journal of the International Menopause Society, Dec. 2006, vol. 9, Nr. 6, Seiten 464-472, Gesamtes Dokument.
Saletu B. et al., "Hormone Replacement Therapy and Vigilance: Double-Blind, Placebo-Controlled EEG-Mapping Studies With an Estrogen-Progestogen Combination (Climodein, Lafamme) Versus Estrogen Alone in Menopausal Syndrome Patients", Maturitas (Ireland), Nov. 20, 2002, vol. 43, Nr. 3, Seiten 165-181, Abstract.
Organon Laboratories Ltd's Application, 1970, (in English).
Awward, J. T. et al., "Abnormal uterine bleeding in the perimenopause," Int. J. Fertil., 1993, vol. 38, pp. 261-269.
Speroff et al., "Clinical Gynecologic Endocrinology and infertility," Lippincott, Williams, and Wilkins: Sixth Edition, 1999, pp. 575-593.
Fraser, I. S. et al., "Treatment of Ovulatory and Anovulatory Dysfunctional Uterine Bleeding With Oral Progestogens," Aust. NZ. J. Obetet. Gynaecol., 1990, vol. 30, No. 4, pp. 353-356.
Hickey, M et al., "Progestogens Versus oestrogens and progestogens for irregular uterine bleeding associated with anovulation," The Cochrane Database of Systematic Review, 2000, vol. 1, pp. 1-9.
Steiner, R. et al., "Abnormal Menstrual Bleeding," Schweiz Rundsch. Med. Prax., 2002, vol. 91, pp. 1967-1974.
Opposition filed by Sandoz International GmbH against EP1787649 on Nov. 26, 2009.
English Translation of Opposition filed by Sandoz International GmbH against EP1787649 on Nov. 26, 2009.
Goretzlehner, G. et al., "Zur Nomenklatur der Zyklusstorungen," Frauenarzt, 2005, vol. 46, No. 1, pp. 34-37.
Tapanainen, J. S., "Medical management of menstrual disorders," International Congress Series, 2004, vol. 1266, pp. 63-68.
Golbs, S. et al., "Clinical Findings with the Oral Contraceptive Combination Ethinylestradiol/ Dienogest in Poland," Methods Find Exp Clin Pharmacol, 2002, vol. 24, No. 9, pp. 585-592.
Golbs, S. et al., "Clinical Findings with the Oral Contraceptive Combination Ethinylestradiol/ Dienogest in the Czech Republic," Methods Find Exp. Clin. Pharmacol., vol. 24, No. 10, pp. 689-696, 2002.
Mueck, A. O. et al., "Effect on biochemical vasoactive markers during postmenopausal hormone response replacement therapy: estradiol versus estradiol/dienogest," Maturitas, 2001, vol. 38, pp. 305-313.
Moller, Svend E., "Deaths of Infants After Triple Vaccine," The Lancet, Sep. 1, 1979, pp. 472.
Carlborg, Lars, "Comparison of Contraception Acceptability of Levonorgestrel and Ethinyl Oestradiol Administered in one Three-Phasic (Trionetta) and one Monophasic (Neovletta) Version" Contraception, May 1983, vol. 27, No. 5, pp. 439-452.
Guenferich, Peter F., "Oxidation of 17 alpha-Ethynylestradiol by Human Liver Cytochrome p-450," Molecular Pharmacology, vol. 33, pp. 500-508, 1988.
Bocker, R. "In vitro interaction of contraception steroids with human liver cytochrome P-450 enzymes," Department of Toxicology and Pharmacology, University of Erlangen-Nurnberg, pp. 141-148, 1991.
Zhu, Bao Ting et al., "The Carcinogenic Activitiy of Ethinyl Estrogens Is Determined by Both Their Hormonal Characteristics and Their Conversion to Catechol Metabolites," Endocrinology, vol. 132, No. 2, 1993, pp. 577-583.
Hirvonen, E. et al., "Oral Contraceptives containing natural estradiol for premenopausal women," Maturitas, 1995, vol. 21, pp. 27-32.
Wenzl, Rene et al., "Ovulation inhibition with a combined oral contraceptive containing 1 mg micronized 17 beta-estradiol," Fertility and Sterility, Oct. 1993, vol. 60, No. 4, pp. 616-619.
Elstein, Max et al., "Studies on Low-dose oral contraceptives: Cervial mucus and plasma hormone changes in relation to circulating d-norgestrel and 17 alpha-ethynyl estradiol concentrations," Fertility and Sterility, Aug. 1976, vol. 27, No. 8, pp. 892-899.
Aktories, K. et al., "Die Beeinflussung des Ovarialzyklus durch verschiedene Typen hormonaler Kontrazeptiva," Geburtsch. U. Frauenheilk, 1976, vol. 36, pp. 318-326.
Kuhl, H. et al., "Aktuelle Entwicklungen in der hormonalen Kontrazeption," Gynakologe, 1992, vol. 25, pp. 231-240.
Watson Pharma, Inc., "About Oral Contraceptives (OCs)," Retrieved from http://www.oralcontraceptives.com/about_benefits.asp on Apr. 5, 2010.
Davis, A. J. et al., "Advances in Contraception," Obstet. Gynecol. Clin. North. Am., Sep. 2000, vol. 27, No. 3, pp. 597-610.
Conrad, J. et al., "Natural Estrogens for Oral Contraception," The Lancet, Sep. 1, 1979, pp. 471.
Bitzer, J., "Kontrazeption and Sexualität," Therapeutische Umschau, Band 61, 1994 Heft 2, pp. 110-114.
Chuong, C.J., M.D., et al., "Management of abnormal uterine bleeding," Am. J. Obstet. Gynecol., Sep. 1996, pp. 787-792.
Davis, A., M.D., et al., "Triphasic Norgestimate-Ethinyl Estradiol for Treating Dysfunctional Uterine Bleeding," Obstet. & Gynecol., vol. 96, No. 6, Dec. 2000, pp. 913-920, XP-002317447.
Dei, M, et al., "Sex Steroids and Libido," The European Jrnl. of Contraception & Reproductive Health Care, vol. 2 (1997) pp. 253-258.
Durán, M., et al., "Efectividad de estradiol valerato/dienogest en la function sexual durante la menopausia (Estudio Venux)," Acta ginecologica, vol. LXIII, (2006) pp. 1-8.
Endrikat, J., et al., "Ovulation inhibition with four variations of a four-phasic estradiol valerate/dienogest combined oral contraceptive: results of two prospective, randomized, open-label studies," Contraception 78 (2008) pp. 218-225.
Gräser, T., et al., "Continuous-combined treatment of the menopause with combinations of oestradiol valerate and dienogest—a dose-ranging study," Maturitas—The European Menopause Journal, 35 (2000) pp. 253-261, XP-002369505.
Gräser, T., et al., "Dienogest as a Progestin for Hormone Replacement Therapy," Drugs of Today, 1999, 35 (Suppl. C) pp. 115-126, XP-008054769.
Kuhl, H., et al., "Kontrazeption," 2. Völlig neubearbeitete Auflage, 19 Abbildungen, 47 Tabellen—1999 Georg Thieme Verlag, Stuttgart—New York. Cover Page and p. 140, titled 12 Kontrazeption bei Problempatientinnen.
L'Oreal's Application in the Appeal Tribunal Before: Mr. Justice Graham and Mr. Justice Whitford—10th and 23rd Jul. 1970. [No. 20] Dec. 31, 1970 R.P.C., pp. 565-579.
Moore, C., et al., "Influence of Dienogest on Ovulation in Young Fertile Women," Clinical Pharmacodynamics, Clin. Drug. Invest. 18 (4), Oct. 1999, pp. 271-278, XP-008054770.
Oettel, M., et al., "The Preclinical and Clinical Profile of Dienogest. A Short Overview," Drugs of Today, 1999, 35 (Suppl. C): pp. 3-12, XP-000909647.
Osmanağaoğlu, M.A., et al., "Effect of different preparations of hormone therapy on sexual dysfunction in naturally postmenopausal women," Climacteric, 2006; 9: pp. 464-472.
Rosenbaum, P., et al., "Inhibition of ovulation by a novel progestogen (drospirenone) alone or in combination with ethinylestradiol," The European Journal of Contraception and Reproductive Health Care, 2000; 5: pp. 16-24.
Saletu, B., et al., "Hormone replacement therapy and vigilance Double-blind, placebo-controlled EEG-mapping studies with an estrogen-progestogen combination (Climodien®, Lafamme®) versus estrogen alone in menopausal syndrome patients," Maturitas—The European Menopause Journal, 43 (2002), pp. 165-181.
Timmer, C. J., et al., "Bioequivalence assessment of three different estrdiol formulations in postmenopausal women in an open, randomized, single-dose, 3-way cross-over study," European Journal of Drug Metabolism and Pharmacokinetics, 1999, vol. 24, No. 1, pp. 47-53.

Strecke, V. J., et al., "Untersuchungen zum Verhalten des Vaginalzytogramms bei Beagle-Hündinnen während toxikologischer Langzeituntersuchungen von Gestagenen[1]," Z. Versuchstierk, 24 (1982), pp. 117-125.

Taubert, H.-D., et al., "Kontrazeption mit Hormonen—Ein Leitfaden für die Praxis," 2., überarbeitete und erweiterte Auflage, 79 Abbildungen, 43 Tabellen—1995 Georg Thieme Verlag Stuttgart—New York. . Cover Page and p. 160, titled Hormanale Kontrazeptiva.

Von Schoultz, B., "Clinical efficacy and safety of combined estradiol valerate and dienogest: a new no-bleed treatment," Climacteric, 2003; 6 (Suppl. 2): pp. 24-32, XP-009062446.

Wellington, K., et al., "Estradiol Valerate/Dienogest," Adis New Drug Profile, Drugs, 2002, 62(3)—Abstract, 2 pages.

Wiegratz, I., et al., "Effect of dienogest-containing oral contraceptives on lipid metabolism," Contraception, 65 (2002), pp. 223-229.

Zimmerman, H., et al., "Pharmacokinetics of Estradiol Valerate 2mg + Dienogest 2mg (Climodien® 2/2) after Single and Repeated Oral Administration in Healthy Postmenopausal Women," Clinical Pharmacokinetics, Clin. Drug. Invest., Aug. 20, 2000, (2), Abstract (1 page).

Zimmerman, H., et al., "Toxicology of Dienogest," Drugs of Today, 1999, 35 (Suppl. C): pp. 13-26.

Written Opinion of the International Searching Authority, along with related papers, issued Jul. 25, 2006 in International Application No. PCT/EP2005/004022 (28 pages).

International Search Report issued Aug. 8, 2007 in International Application No. PCT/EP2006/008626 (4 pages).

Written Opinion of the International Searching Authority issued Aug. 8, 2007 in International Application No. PCT/EP2006/008626 (6 pages).

Search Report issued Apr. 30, 2007 in ROC (Taiwan) Patent Application No. 094109222 (1 page).

International Search Report, along with related papers, issued Jan. 4, 2007 in International Application No. PCT/EP2006/009867 (11 pages).

Teichmann, A.T., "Dienogest: Pre-Clinical and clinical results for the new Gestogen," Walter de gruyter, Berlin/New York, p. 101, 1995.

Pierson, R.A., et a l., "Ortho Evar™ /Evra™ versus oral contraceptives: follicular development and ovulation in normal cycles and after intentional dosing error," Fertility and Sterility, vol. 80, No. 1, Jul. 2003, pp. 34-42.

Chemical Translations, Dr. S. Edmund Berger, translation from German to English of U.S. Appl. No. 11/873,595, by S. Zeun, et al., 9 pages and certificate of Accuracy, 2008.

Akerlund et al., "Comparative profiles of reliability, cycle control and side effects of two oral contraceptive formulations containing 15Oug desogestrel and either 30 ug or 20 ug ethinyl oestradiol," Brit J. Obstet Gynecol, 1993, vol. 100, pp. 832-838.

Asted, B. et al., "Clinical trial of a new oral contraceptive pill containing the natural oestrogen 17 beta-oestradiol," British J. Of Ob Gyn., Sep. 1979, vol. 86, No. 9, pp. 732-736.

Astedt, B. et al., "The natural oestrogenic hormone oestradiol as a new component of combined oral contraceptives," British Medical Journal, 1977.

Bayer, S. R. et al., "Clinical Manifestations and Treatment of Dysfuntional Uterine Bleeding," JAMA, Apr. 14, 1993, vol. 269, No. 14.

Climodien, EU SmPC, 2008.

Clinical Study Report No. A39818, viits from Mar. 2, 2005 to Jul. 20 2007, Bayer Healthcare.

Csemiczky, G. et al., The pharmacodynamic Effects of an oral contraceptive containing 3 mg micronized 17 beta-estradiol and 0.150 mg desogestrel for 21 days, followed by 0.030 mg desogestrel only for 7 days, Contraception, 1996, vol. 54, No. 6, pp. 333-338.

Darney, P. D. et al., "Contraception-associated menstrual problems: etiology and management," Dialogues in Contraception, 1998, vol. 5, No. 5, pp. 1-6.

Darney, P. et al., "Safety and efficacy of a triphasic oral contraceptive containing desogestrel: results of three multicenter trials," Contraception, 1993, vol. 48, No. 4, pp. 323-337.

Declaration by Maria de las Nieves Fernandez Hernando, Apr. 12, 2001.

Dittgen et al., U.S. Appl. No. 08/738,314 filed Oct. 25, 1996, Declaration filed Apr. 13, 2000.

Dittgen et al., U.S. Appl. No. 08/738,314 filed Oct. 25, 1996, Amendment Jan. 7, 2000, 13 pages.

Dittgen et al., U.S. Appl. No. 09/648,858 filed Aug. 25, 2000, Amendment Dec. 22, 2003, 8 pages.

Dittgen et al., U.S. Appl. No. 09/950,915 filed Sep. 12, 2001, Amendment Dec. 18, 2003, 12 pages.

Dittgen et al., U.S. Appl. No. 09/950,915 filed Sep. 12, 2001, Amendment Aug. 19, 2004.

Drugs of the Future, 2001, vol. 26, No. 6, pp. 577-625.

Endrikat et al., "A twelve-month comparative clinical investigation of two low-dose oral contraceptives containing 20 micrograms ethinylestradiol/75 micrograms gestodene and 30 micrograms ethinylestradiol/75 micrograms gestodene, with respect to efficacy, cycle control, and tolerance," Contraception, 1997, vol. 55, No. 3, pp. 131-137.

Endrikat, J. et al., "Multicenter, comparative study of cycle control, efficacy and tolerability of two low dose oral contraceptives containing 20 microg ethinylestradiol/500 microg levonorgestrel and 20 microg ethinylestradiol/500 microg norethisterone," Contraception, 2001, vol. 64, No. 1, pp. 3-10.

English Abstract of DE 3 341 638, Hesslinger, Three-phase product for contraception—Espacenet, Publication Date: May 3, 1984.

Excerpts from U.S. Appl. No. 10/891,729 file history, Reasons for Allowance of Jun. 5, 2009, Amendment of Feb. 13, 2009, Jul. 22, 2008, Oct. 18, 2004, Official Actions of Nov. 14, 2008 and Apr. 2, 2008, Terminal Disclaimer Feb. 13, 2009.

FDA Approval Letter (with attachments) for Natazia, May 2010.

Foster, R. H. et al., Drugs, 1998, vol. 56, pp. 825-833.

Fruzzetti, F. et al., "Review of clinical experience with estradiol in combined oral contraceptives," Contraceptions, 2010; 81(1): 8-15.

Graser et al., "Comparison of the efficacy and endometrial safety of two estradiol valerate/dienogest combinations and Kliogest for continous combined hormone replacement therapy in postmenopausal women," Climacteric, 2000, vol. 3, No. 2, pp. 109-118.

Graser, T. et al., "Lafamme, A new oral preparation " Drugs of Today, 2001, vol. 37, Suppl. G, pp. 17-27.

Graser, T. et al., "Organ targeting with the oral progestin dienogest," Drugs of Today, 1996, vol. 32, pp. 43-55.

Hagstad, A. et al., "Effects of two estradiol/norgestrel combinations on the ovulatory pattern and on sex hormone binding globulin capacity in women around forty years of age," Acta Obstet Gynecol Scand, 1984, vol. 63, pp. 321-324.

Hirvonen, E. et al., "A multicenter trial with a new OC," Adv. Contracept., 1990, vol. 6, pp. 248.

Hirvonen, E. et al., "New natural oestradiol/cyproterone acetate oral contraceptives for pre-menopausal women," Maturitas, 1988, vol. 10, No. 3, pp. 201-213.

Hoffmann, H. et al., "Alternatives for the replacement of ethinylestradiol by natural 17Beta-estradiol in dienogest-containing oral contraceptives," Drugs of Today, 1999, vol. 35, Suppl. C, pp. 105-113.

Hoffmann, H. et al., "Approaches to the replacement of ethinylestradiol by natural 17beta-estradiol in combined oral contraceptives," Exp. Toxic Pathol, 1998, vol. 50, pp. 458-464.

Kivinen, S. et al., "Efficacy and tolerability of a combined oral contraceptive containing 17beta-estradiol and desogestrel," Eur. J. Contracept Reprod Health Care, 1996, vol. 1, pp. 183.

Kwiecien, M. et al., "Bleeding patterns and patient acceptability of standard or continous dosing regiements of a low-dose oral contraceptives: a randomized trial," Contraception, 2003, vol. 67, pp. 9-13.

Lox, C. D., "Biochemical effects in women following one year's exposure to a new triphasic contraceptive—I. Chemistry profiles," General Pharmacology, Mar. 1996, vol. 27, No. 2, pp. 367-370.

Miller et al., "Continuous combination oral contraceptives pills to eliminate withdrawal bleeding: A randomized tiral" Obstetrics and Gynecology, Apr. 2003, vol. 101, No. 4, pp. 653-661.

Moore et al., 1995, pp. 161-170.

Moore, C. et al., "Different alternatives for the substitution of ethinylestradiol in oral contraceptives," Jenapharm, 1998, pp. 25-35.

Public Assessment Report of the Medicines Evalution Board, Qlaira, 2009.

Rosenbaum, P. et al., "Inhibition of ovulation by a novel progestogen (drospirenone) alone or in combination with ethinylestradiol.," European Journal of Contraception and Reproductive Health Care, 2000, vol. 5, No. 1, pp. 16-24.

Rudolph, I. et al., "Influence of a continous combined . . ." Climateric, 2004, vol. 7, pp. 301-311, online publication, Jan. 9, 2004.

Schubert, W. et al., "Ovulation inhibition with 17beta-estradiol cyclo-octyl acetate and desogestrel," Acta Obstet Gynecol, 1987, vol. 66, pp. 543-547.

Schwarz, B. E. et al., "Reference periold analysis of vaginal bleeding with triphasic oral contraceptive agents containing norethindrone or levonorgestrel: a comparative study," International Journal of Fertility, 1992, vol. 37, No. 3, pp. 176-182.

Serup, J. et al., "Effectivity and Acceptabilityof oral contraceptives containing natural and artificial estrogens in combination with a gestagen. A controlled double-blind investigation" Acta Obstet Gynecol Scand, 1981, vol. 60, No. 2, pp. 203-206.

Taubert et al., Kontrazeption mit Hormones, Thieme Verlag, 1995, pp. 397-398.

Teichmann, A. et al., "Pharmacy of estradiol valerate/dienogest," Climacteric, 2003, vol. 6, Suppl. 2, pp. 17-23.

Tuimala, R. et al., Acta Obstet Gynecol Scand, 1987, vol. 144, pp. 7-12.

Udoff et al., "Combined continuous hormone replacement . . .," Obstetrics and Gynecology, Aug. 1995, vol. 86, No. 2, pp. 306-316.

Umbreit et al., "Ovulation-inhibiting composition for . . .," Data Retrieved from the Espacenet Database, Publication Date: Nov. 10, 1994; English Abstract of DE-4 339 934.

Wiegratz et al., "Effects of four different oral contraceptives on various sex hormones and serum-binding globulins," Contraception, vol. 67, No. 1, pp. 25-32, 2003.

World Health Organization Task Force on Oral Contraception, Contraception, 1980, vol. 21, pp. 445-459.

Wright, J. V. et al., "Comparative Measurements of Serum Estriol. Estradiol . . .," Altern med. Rev, Aug. 1999, vol. 4, No. 4, pp. 266-270.

Zimmermann, T. et al., "The efficacy and tolerability of Valette . . .," Eur. J. Contracept. Reprod. Health Care, Sep. 1999, vol. 4, No. 3, pp. 155-164.

* cited by examiner

USE OF ESTRADIOL VALERATE OR 17β-ESTRADIOL IN COMBINATION WITH DIENOGEST FOR ORAL THERAPY TO MAINTAIN AND/OR INCREASE FEMININE LIBIDO

RELATED APPLICATION DATA

This application is a non-provisional application claiming the benefit of priority of U.S. Provisional Application No. 60/917,154, filed May 10, 2007, under 35 U.S.C.§119(e).

TECHNICAL FIELD

The invention relates to the use, optionally together with oral contraception, of estradiol valerate or 17β-estradiol (estradiol) in combination with 17α-cyanomethyl-17-β-hydroxyestra-4,9-dien-3-one (dienogest) in a multistage or single-stage combination preparation for oral therapy to maintain and/or increase feminine libido. The total number of daily dose units of the multistage combination and a pharmaceutically harmless placebo or of the single-stage combination and optionally the pharmaceutically harmless placebo-containing or placebo- and hormone-free daily dose units equals 28.

PRIOR ART

Feminine libido is a very complicated occurrence influenced by numerous hormonal and psycho-social factors. It has been known for a long time that at the beginning of the climacterium women can experience a reduction in sexual desire. The decreasing endogenous estradiol level and reduced androgen level are discussed as reasons of this phenomenon. It is less well known that the intake of conventional combination of oral contraceptives and the so-called "Progestin-only-Pills (POPs) can bring about an acquired loss/decrease in libido. Such disorders are combined under the expression "acquired OC-associated hypoactive sexual desire disorder (HSDD)" (Blitzer: "Kontrazeption und Sexualität" [Contraception and Sexuality], Therapeutische Umschau, vol. 51, 1994, issue 2, 110-114). The reason for this has not been explained, and different theses are under discussion. At this time, this observed phenomenon cannot be sufficiently prevented. (Sex Steroids and Libido, The European Journal of Contraception and Reproductive Health Care, 1997, 253-258).

PRESENTATION OF THE INVENTION

The object of the invention is to find possibilities whereby feminine libido can be maintained or increased.

According to the invention, this objective is reached by the use of estradiol valerate or estradiol in combination with 17α-cyanomethyl-17-β-hydroxyestra-4,9-dien-3-one (dienogest) to prepare a multistage combination preparation or a single-stage combination preparation for oral therapy to maintain and/or increase feminine libido.

Surprisingly, we have now found that oral contraception is associated with the attainment of or increase in feminine libido.

Advantageously, estradiol valerate or estradiol in combination with 17α-cyanomethyl-17-β-hydroxyestra-4,9-dien-3-one (dienogest) are used, optionally together with oral contraception, for oral therapy to maintain or increase feminine libido. In this case, a first stage of 2 daily dose units of estradiol valerate contains up to 3 mg of estradiol valerate or less than 3 mg of estradiol, a second stage consists of 2 groups of daily dose units of which the first group contains 5 daily dose units of a combination of 2 mg of estradiol valerate or less than 2 mg of estradiol and 2 mg of dienogest and the second group contains 17 daily dose units of a combination of 2 mg of estradiol valerate or less than 2 mg of estradiol and 3 mg of dienogest, a third stage consists of 2 daily dose units with 1 mg of estradiol valerate or less than 1 mg of estradiol, and an additional stage consists of 2 daily dose units of a pharmaceutically harmless placebo for preparing a multistage combination preparation with a total number of 28 daily dose units.

Advantageously, an amount of 3 mg or less of estradiol valerate or estradiol in combination with 2.00 mg or less of 17α-cyanomethyl-17-β-hydroxyestra-4,9-dien-3-one (dienogest) are also used, optionally together with oral contraception, to prepare a single-stage combination preparation for oral therapy to maintain and/or increase feminine libido. The single-stage combination contains 28 or 21, 22, 23, 24, 25, 26, 27 daily dose units with a constant amount of dienogest and estradiol valerate or dienogest and 17β-estradiol, and 7, 6, 5, 4, 3, 2, 1 pharmaceutically harmless placebo-containing or placebo- and hormone-free daily dose units, so that the total number of daily dose units equals 28.

Placebo- and hormone-free daily dose units correspond to pill-free days. It is also conceivable to replace part of the amount of estradiol valerate used in accordance with claims 1 and 3 with ethinylestradiol so that the amount of estrogens used in the single-stage combination preparation is not equal to or less than 3 mg of estradiol valerate but, for example, equal to 2 mg or 1 mg, the said combination always containing 10 μg of ethinylestradiol.

It is also advantageous to administer the single-stage preparation in a long-term cycle, the said cycle consisting of
a first stage of a combination of 1.0-2.0 mg of dienogest and 3 mg of estradiol valerate or less than 3 mg of 17β-estradiol or of a combination of 1.0-2.0 mg of dienogest and 2 mg or 1 mg of estradiol valerate and 10 μg of ethinylestradiol, up to n×21 daily dose units with n=2 to 5 containing a constant amount of dienogest and estradiol valerate or of dienogest and ethinylestradiol, and 17β-estradiol,
a second stage after n=2 to 5 consisting of 7 pill-free, namely placebo- and hormone-free or 7 placebo-containing daily dose units.

It is particularly advantageous if the single-stage combination preparation with 21-27 daily dose units of dienogest and estradiol valerate and optionally ethinylestradiol or 17β-estradiol contains from 1 to 7 placebo- and hormone-free or 1 to 7 placebo-containing daily dose units so that the total number of daily dose units equals 28, and after that is used in the above-said long-term cycle.

Studies Concerning the Efficacy of the Claimed Formulation

Clinical studies are carried out with an orally administered multistage combination of estradiol valerate and dienogest. In these studies the first stage consists of 2 daily dose units of up to 3 mg of estradiol valerate and the second stage of 2 groups of daily dose units. The first groups of this second stage consist of 5 daily does units of a combination of 2 mg of estradiol valerate and 2 mg of dienogest and the second group of 17 daily dose units of a combination of 2 mg of estradiol valerate and 3 mg of dienogest. The third stage contains 2 daily dose units with 1 mg of estradiol valerate, and another stage consists of 2 daily dose units of a pharmaceutically harmless placebo. The total number of days of an administration cycle of the multistage combination and the pharmaceutically harmless placebo amounts to 28 days (A).

In a randomized, double-blind clinical study, 800 women between the ages of 18 and 50 years (400 in the age group of 18 to 35 years and 400 in the age group between 36 to 50 years) and who give their written consent to participate in the study receive two different courses of treatment.

Treatment (A) is erformed with the afore-said combination.

The second treatment (B) is performed with Miranova (20 µg of ethinylestradiol and 0.1 mg of levonorgestrel).

The study includes a pretreatment cycle, 7 treatment cycles and a post-treatment cycle (follow-up stage).

The invention claimed is:

1. A method for maintaining or increasing feminine libido comprising orally administering to a woman
   one oral dosage unit comprising 3 mg of estradiol valerate daily for 2 days,
   then one oral dosage unit comprising 2 mg of estradiol valerate and 2 mg of dienogest daily for 5 days,
   then one oral dosage unit comprising 2 mg of estradiol valerate and 3 mg of dienogest daily for 17 days,
   then one oral dosage unit comprising 1 mg of estradiol valerate daily for 2 days, and
   then one oral dosage unit comprising a pharmaceutically acceptable placebo daily for 2 days,
   wherein the woman's libido is maintained or increased.

2. A method of claim 1 wherein the woman's libido is increased.

3. A method of claim 1 wherein the woman's libido is maintained.

4. A method for oral contraception and maintaining or increasing feminine libido comprising orally administering to a woman
   one oral dosage unit comprising 3 mg of estradiol valerate daily for 2 days,
   then one oral dosage unit comprising 2 mg of estradiol valerate and 2 mg of dienogest daily for 5 days,
   then one oral dosage unit comprising 2 mg of estradiol valerate and 3 mg of dienogest daily for 17 days,
   then one oral dosage unit comprising 1 mg of estradiol valerate daily for 2 days, and
   then one oral dosage unit comprising a pharmaceutically acceptable placebo daily for 2 days,
   wherein the woman's libido is maintained or increased.

5. A method of claim 4 wherein the woman's libido is increased.

6. A method of claim 4 wherein the woman's libido is maintained.

* * * * *